United States Patent
Hurson

(10) Patent No.: US 6,733,291 B1
(45) Date of Patent: May 11, 2004

(54) IMPLANT WITH INTERNAL MULTI-LOBED INTERLOCK

(75) Inventor: Steven M. Hurson, Yorba Linda, CA (US)

(73) Assignee: Nobel Biocare USA, Inc., Yorba Linda, CA (US)

( * ) Notice: Subject to any disclaimer, the term of this patent is extended or adjusted under 35 U.S.C. 154(b) by 0 days.

(21) Appl. No.: 09/670,708

(22) Filed: Sep. 27, 2000

Related U.S. Application Data

(60) Provisional application No. 60/156,198, filed on Sep. 27, 1999.

(51) Int. Cl.$^7$ .................................................. A61C 8/00
(52) U.S. Cl. ............................................................ 433/173
(58) Field of Search ................................. 433/173, 174, 433/175, 176

(56) References Cited

U.S. PATENT DOCUMENTS

| | | | | |
|---|---|---|---|---|
| 4,713,003 A | 12/1987 | Symington et al. | ......... | 433/173 |
| 4,826,434 A | 5/1989 | Krueger | ....................... | 433/174 |
| 4,960,381 A | 10/1990 | Niznick | ...................... | 433/174 |
| 5,076,788 A | 12/1991 | Niznick | ...................... | 433/173 |
| 5,195,892 A | 3/1993 | Gersberg | .................... | 433/174 |
| 5,328,371 A | 7/1994 | Hund et al. | ................. | 433/173 |
| 5,439,381 A | 8/1995 | Cohen | ........................ | 433/173 |
| 5,580,246 A | 12/1996 | Fried et al. | ................. | 433/172 |
| 5,584,629 A | 12/1996 | Bailey et al. | ............... | 411/178 |
| 5,725,375 A | 3/1998 | Rogers | ....................... | 433/172 |
| 5,782,918 A * | 7/1998 | Klardie et al. | ............... | 623/16 |
| 5,810,590 A | 9/1998 | Fried et al. | ................. | 433/172 |
| 5,823,776 A | 10/1998 | Duerr et al. | ................ | 433/173 |
| 5,915,968 A | 6/1999 | Kirsch et al. | .............. | 433/173 |
| 6,116,904 A | 9/2000 | Kirsch et al. | .............. | 433/173 |
| 6,394,806 B1 * | 5/2002 | Kumar | ....................... | 433/173 |

OTHER PUBLICATIONS

Picture of Prior Art, Dental Implant. Solid before Sep. 27, 1999.

* cited by examiner

*Primary Examiner*—Kevin Shaver
*Assistant Examiner*—Melba Bumgarner
(74) *Attorney, Agent, or Firm*—Knobbe, Martens, Olson & Bear, LLP.

(57) ABSTRACT

A dental implant for supporting a dental prosthesis comprises a body portion and a top surface. The implant further comprises an internal cavity with an opening located at the top surface. The internal cavity comprises an interlock chamber having a depth measured from the top surface equal to a first distance. The interlock chamber comprising a cylindrical portion and plurality of semi-circular channels arranged around a periphery of the cylindrical portion. A threaded chamber that includes threads is located below the post-receiving chamber. The cylindrical portion has a first radius and the channels have a second radius, a ratio of the first radius to the second radius being between approximately 4:1 and 2:1.

21 Claims, 6 Drawing Sheets

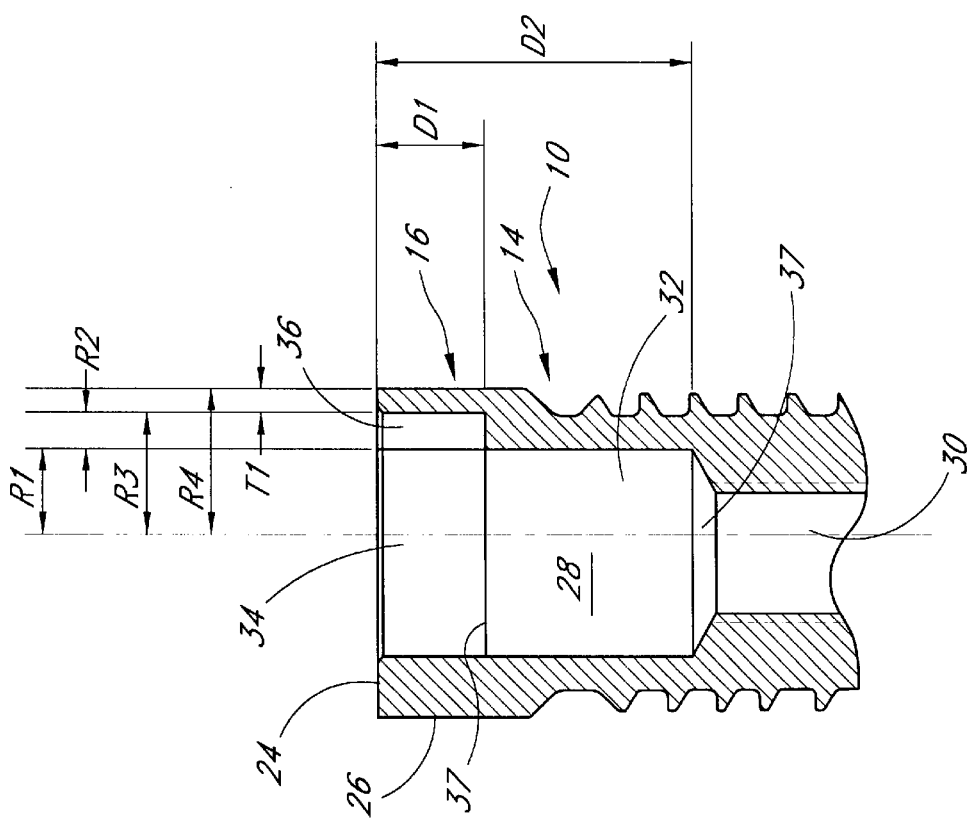
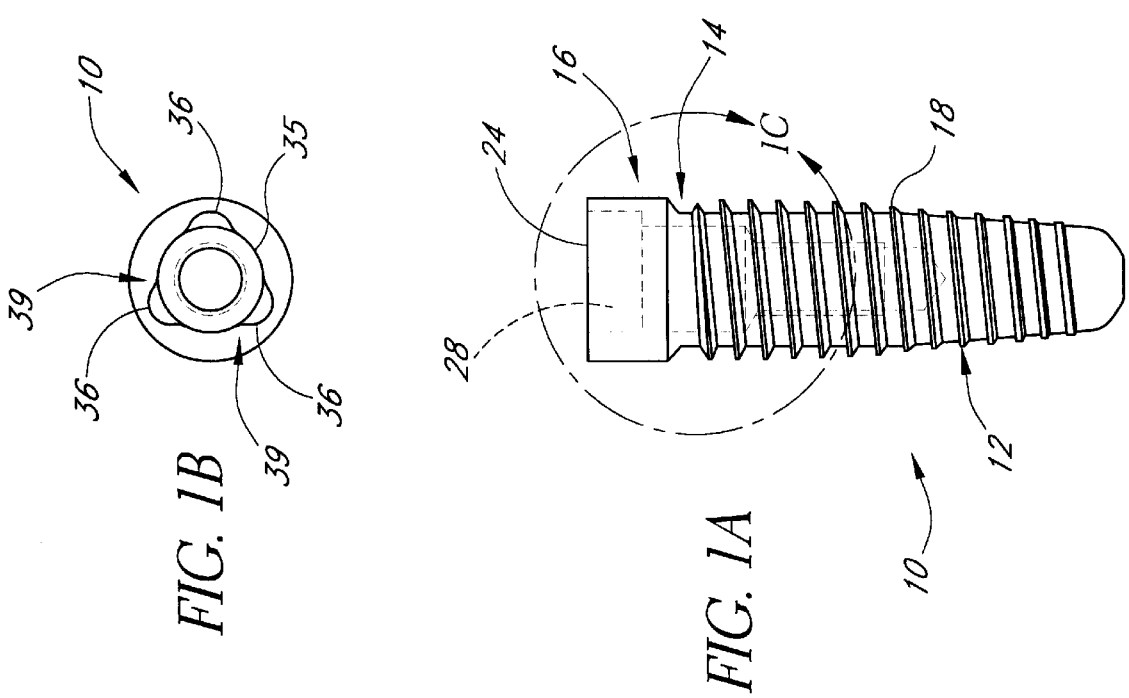

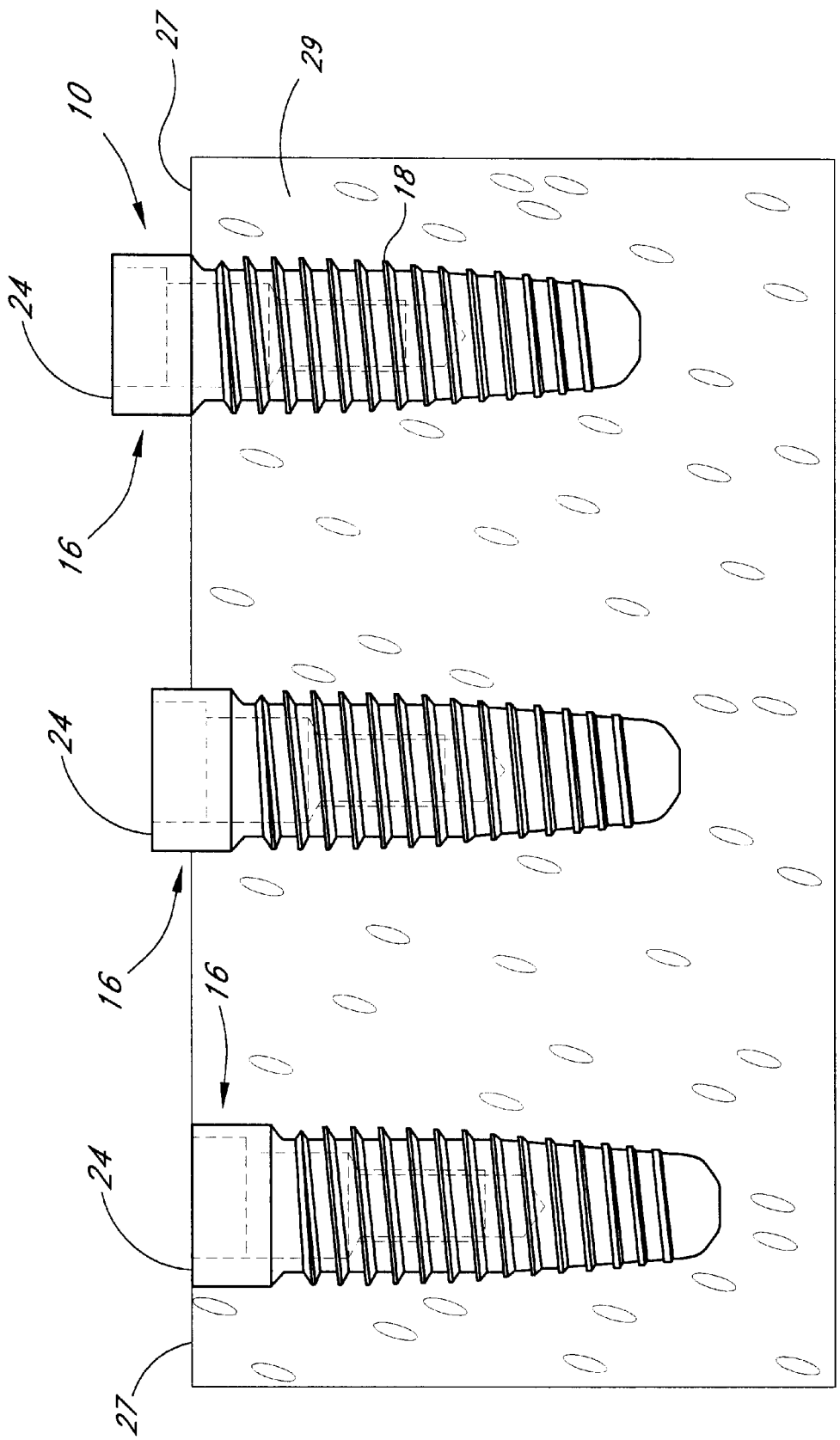

IMPLANT WITH INTERNAL MULTI-LOBED INTERLOCK

CROSS REFERENCE TO RELATED APPLICATIONS

The present application claims priority and benefit under 35 U.S.C. §119(e) of U.S. Provisional Patent Application Serial No. 60/156,198, filed Sep. 27, 1999.

BACKGROUND OF THE INVENTION

1. Field of the Invention

The present invention relates generally to dental implants and, more particularly, to an improved implant with an improved internal interlock for supporting other dental implant components with corresponding interlock structures.

2. Description of the Related Art

Implant dentistry involves the restoration of one or more teeth in a patient's mouth using artificial components. Such artificial components typically include a dental implant and a prosthetic tooth and/or a final abutment that is secured to the dental implant. Generally, the process for restoring a tooth is carried out in three stages.

Stage I involves implanting the dental implant into the bone of a patient's jaw. The oral surgeon first accesses the patient's jawbone through the patient's gum tissue and removes any remains of the tooth to be replaced. Next, the specific site in the patient's jaw where the implant will be anchored is widened by drilling and/or reaming to accommodate the width of the dental implant to be implanted. Then, the dental implant is inserted into the hole in the jawbone, typically by screwing, although other techniques are known for introducing the implant in the jawbone.

The implant itself is typically fabricated from pure titanium or a titanium alloy. Such materials are known to produce osseointegration of the fixture with the patient's jawbone. The dental implant fixture also typically includes a hollow threaded bore through at least a portion of its body and extending out through its proximal end which is exposed through the crestal bone for receiving and supporting the final tooth prosthesis and/or various intermediate components or attachments.

After the implant is initially installed in the jawbone, a temporary healing cap is secured over the exposed proximal end in order to seal the internal bore. The patient's gums are then sutured over the implant to allow the implant site to heal and to allow desired osseointegration to occur. Complete osseointegration typically takes anywhere from four to ten months.

During stage II, the surgeon reassesses the implant fixture by making an incision through the patient's gum tissues. The healing cap is then removed, exposing the proximal end of the implant. Typically, an impression coping in attached to the implant and a mold or impression is then taken of the patient's mouth to accurately record the position and orientation of the implant within the mouth. This is used to create a plaster model or analogue of the mouth and/or the implant site and provides the information needed to fabricate the prosthetic replacement tooth and any required intermediate prosthetic components. Stage II is typically completed by attaching to the implant a temporary healing abutment or other transmucosal component to control the healing and growth of the patient's gum tissue around the implant site.

Stage III involves fabricating and placement of a cosmetic tooth prosthesis to the implant fixture. The plaster analogue provides laboratory technicians with a model of the patient's mouth, including the orientation of the implant fixture relative to the surrounding teeth. Based on this model, the technician constructs a final restoration. The final step in the restorative process is replacing the temporary healing abutment with the final restoration.

As mentioned above, the implant typically includes a hollow threaded bore for receiving and supporting the final tooth prosthesis and/or various intermediate components or attachments. The implant also typically includes anti-rotational means, which are typically located on the proximal end of the implant. These anti-rotational means are designed to mate with corresponding anti-rotational means formed on the various mating components (e.g., a healing abutments and/or an impression coping). These anti-rotational means primarily serve to prevent relative rotation between the mating component and the implant.

Such anti-rotational/indexing means frequently take the form of a hexagonal boss or recess ("hex") formed on the proximal portion of the implant. For externally threaded implants, the hex may also be used to engage a driving tool for driving the implant into an internally threaded bore or osteotomy prepared in the patient's jawbone (mandible or maxilla). When the implant is fully installed in a patient's jawbone, the hex or other indexing means is typically exposed through the crestal bone so that accurate indexing may be provided between the implant and the final prosthesis and/or various intermediate mating prosthetic components.

SUMMARY OF THE INVENTION

One aspect of the present invention includes the realization that prior art anti-rotational means typically include sharp corners. When the implant and mating component are subjected to a rotational force, these sharp corners are subject to high concentrations of stress. The high stress concentrations can cause the sharp corners to chip or wear away. This can cause the anti-rotational means to take on a circular shape, which reduces the ability of the anti-rotational means to resist rotation. The chipping or wearing away can also result in fitting errors between the implant and the mating components. In some cases, the high stress concentrations can also cause the implant to crack at or near the corners of the anti-rotational means thereby shortening the life of the implant.

Another aspect of the present invention includes the realization that prior art anti-rotational means typically offer little resistance to lateral forces. That is, prior art anti-rotational means typically do not prevent the mating component from "tipping" off the implant. Furthermore, prior art anti-rotational means typically provide little or no tactile feedback to the oral surgeon to indicate that the mating component is properly seated in the implant.

Yet another aspect of the present invention is the recognition that traditional anti-rotation means, such as a hexagonal recess, are difficult to machine. Specifically, a special reciprocating tool, such as a broach, typically must be used to form a hexagonal recess.

Accordingly, it is a principle object and advantage of the present invention to overcome some or all of the above-mentioned limitations in the prior art. Thus, one aspect of the present invention provides for a dental implant for supporting a dental prosthesis comprises a body portion and a top surface. The implant further comprises an internal cavity with an opening located at the top surface. The internal cavity comprises an interlock chamber having a depth measured from the top surface equal to a first distance. The interlock chamber comprising a cylindrical portion and plurality of semi-circular channels arranged around a periphery of the cylindrical portion. A threaded chamber that includes threads is located below the post-receiving chamber. The cylindrical portion has a first radius and the channels have a second radius, a ratio of the first radius to the second radius being between approximately 4:1 and 2:1.

Another aspect of the present invention provides for a prosthodontic assembly for installing a prosthetic tooth. The prosthodontic assembly comprises a first prosthodontic component and a second prosthodontic component. The first prosthodontic component comprising a body portion and a top surface. The first prosthodontic component further comprising an internal cavity with an opening located at the top surface. The internal cavity comprising an interlock chamber having a depth measured from the top surface equal to a first distance. The interlock chamber comprising a cylindrical portion with a plurality of semi-circular channels arranged around a perimeter of the cylindrical portion. A threaded chamber that includes threads is located below the interlock chamber. The cylindrical portion has a first radius and the channels have a second radius. A ratio of the first radius to the second radius is between approximately 4:1 and 2:1. The second prothodontic component comprising an interlock area comprising a plurality of semi-circular protrusions configured to mate with channels of the first prosthodontic component.

Yet another aspect of the present invention provides for a dental implant for supporting a dental prosthesis. The dental implant comprising a body portion and a top surface. The implant further comprising an internal cavity with an opening located at the top surface. The internal cavity comprising an interlock chamber having a depth measured from the top surface equal to a first distance. A threaded chamber that includes threads and is located below the post-receiving chamber. The interlock channel being formed as a single continues curve having substantially no internal corners.

Still yet another aspect of the present invention provides for a prosthodontic assembly for installing a prosthetic tooth. The prosthodontic assembly comprises a first prosthodontic component and a second prosthodontic component. The first prosthodontic component comprising a body portion and a top surface. The first prosthodontic component further comprising an internal cavity with an opening located at the top surface. The internal cavity comprising an interlock chamber having a depth measured from the top surface equal to a first distance. The interlock chamber being formed as a single continuos curve having substantially no internal corners. A threaded chamber that includes threads is located below the post-receiving chamber. The second prothodontic component comprising an interlock area having a shape that corresponds to the shape of the interlock chamber.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

These and other features of this invention will now be described with reference to the drawings of a preferred embodiment which is intended to illustrate and not to limit the invention. The drawings contain the following figures.

FIG. 1A is a side view of a dental implant having certain feature and advantages according to the present invention;

FIG. 1B is a top plan view of the dental implant of FIG. 1A;

FIG. 1C is a cross-sectional view of the dental implant of FIG. 1A;

FIGS. 1D–F are side views of the dental implant of FIG. 1A inserted into a patient's jawbone at different depths;

DETAILED DESCRIPTION OF THE PREFERRED EMBODIMENT

Figure 2D:
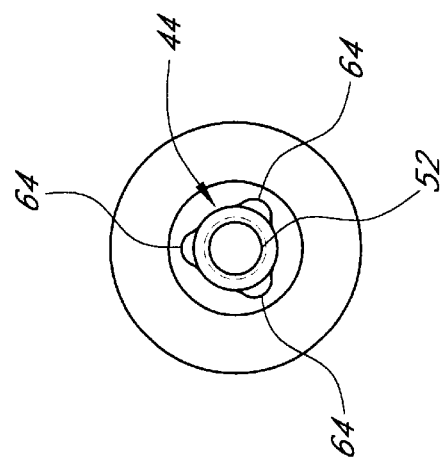
FIG. 2D is a bottom plan view of the abutment of FIG. 2A.

FIGS. 1A–1C illustrate a preferred embodiment of a dental implant 10 having certain features and advantages in accordance with the present invention. As will be explained below, the implant 10 is configured to receive and support one or more dental attachments or components such as, for example, healing caps, impression copings, temporary abutments, and permanent abutments. The implant 10 is preferably made of a dental grade titanium alloy, although other suitable materials can be used.

As best seen in FIG. 1A, the outer surface of the implant 10 preferably includes a body portion 12, a neck 14, and a collar 16. The body portion 12 of the implant 10 is preferably tapered and includes threads 18 that match preformed threads made along the inner surface of the patient's jawbone (not shown). However, it should be appreciated that the body portion 12 can be configured so as to be self-tapping. It should also be appreciated that although the illustrated body portion 12 is tapered or conical, the body portion 12 could also be substantially cylindrical. Finally, the body portion 12 could be unthreaded if the surgeon prefers to use an unthreaded implant.

The body portion 12 of the implant 10 is also preferably acid-etched. Acid-etching produces a rougher surface, which increases the surface area of the body portion 12. The increased surface area promotes osseointegration. Alternatively, the body portion 12 of the implant can be coated with a substance that increases the surface area of the body portion 12. Calcium phosphate ceramics, such as tricalcium phosphate (TCP) and hydroxyapatite (HA), are particularly suitable materials.

As best seen in FIG. 1C, the neck 14 lies between the body portion 12 and the collar 16. The neck 14 preferably has a diameter that is less than the diameter of the collar 16. The collar 16 of the implant is substantially cylindrical and has a top surface 24 that is substantially flat. The collar 16 is defined in part by a vertical side wall 26 that is preferably greater than 1 millimeter in length. In the preferred embodiment, the length of the collar is approximately 2 millimeters.

The neck 14 and the collar 16 form a "variable placement zone". The length and configuration the variable placement zone allows for "variable positioning" of the dental implant 12. That is, the surgeon can vary the height of the implant 10 with respect to the crest of the jawbone. For example, as shown in FIG. 1F, the implant 10 can be placed supra-crestally (i.e., the top surface 24 of the implant 10 is positioned above the crest 27 of the jawbone 29) without exposing the threads 18 of the body region 12. In this arrangement the collar 16 extends through the gums and acts as the temporary healing abutment thereby saving the surgeon and the patient time and money by eliminating stage II surgery. Alternatively, the surgeon can place the top surface 24 of the implant 10 level with the alveolar crest (i.e., the tooth socket in the jawbone) for esthetics (see FIG. 1E). In yet another alternative arrangement, the surgeon can submerge the collar 16 into the jawbone such that the top surface 24 lies flush with the crest of the jawbone (see FIG. 1D). In this arrangement, the surgeon can utilize the standard three stage process described above.

It should, however, be noted that several advantages of the present invention can be achieved with an implant 10 that (i) does not include a variable placement zone or (ii) includes variable placement zone that is smaller or larger than the preferred embodiment. For example, several advantages of the present invention can be achieved with an implant without the neck 14 and/or the collar 16. Similarly, the neck 14 and/or collar 16 can have dimensions that are smaller or larger than the illustrated embodiment. However, the illustrated embodiment, with the neck region 14 and collar 16, is preferred because it best allows for the flexibility described above.

As best seen in FIG. 1C, the implant 10 includes an internal socket 28. The socket 28 includes a threaded chamber 30 and an interlock chamber 34. The threaded chamber 30 is threaded and preferably has a diameter that is less than the interlock chamber 34.

With reference to FIGS. 1B and 1C, the interlock chamber 34 includes a substantially cylindrical portion 35. The interlock chamber 34 also includes a plurality of channels 36, which prevent the rotation of a dental component. Preferably, the interlock chamber 34 includes three semi-circular channels 36, which are arranged along the periphery of the cylindrical portion 35. More preferably, each channel 36 is located approximately 120 degrees apart from each other. The channels 36 preferably extend from the top surface 24 to the bottom 37 of the cylindrical portion 35. That is, the channels 36 have the same depth as the cylindrical portion 35.

The cylindrical portion 35 has a first radius R1 and the semi-circular channels 36 have a second radius R2. The ratio $\alpha_1$, of the first radius R1 to the second radius R2 preferably is between 2:1 and 4:1. In the preferred embodiment the ratio a, is about 3:1. This arrangement is preferred to minimize the stress concentrations in the dental implant 10, as will be explained below. To reduce stress concentrations further, the interfaces 39 between the channels 36 and the cylindrical portion 35 are preferably rounded.

The interlock chamber 34 is preferably dimensioned to be as large as possible without significantly compromising the structural integrity of the vertical side wall 26. This arrangement is preferred because it increases the surface area of the interlock chamber 34. The larger surface area results in a more stable connection between the implant 10 and the mating dental component. Accordingly, the interlock chamber 34 has a third radius R3, which is approximately equal to the first radius R1 plus the second radius R2. The third radius R3 is sized such that the thickness T1 (i.e., the radius R4 of the implant minus R3) of the vertical wall 26 is greater than a minimum value, which provides sufficient structural integrity for the implant 10. For an implant made of dental grade titanium alloy, the preferably minimum value is approximately 0.4–0.8 millimeters. Another preferred aspect of the shape of the interlock chamber 34 is the ratio between the radius R4 of the implant 10 and the radius R2 of the channels 36. More specifically, the ratio between the radius R4 of the implant and the radius R2 of the channels 36 is preferably between 4:1 to 5:1. In the preferred embodiment, the ratio is about 4.5:1.

The internal socket 28 also preferably includes a post-receiving chamber 32, which lies between the interlock chamber 34 and the threaded chamber 30. The post-receiving chamber 32 is preferably substantially cylindrical. The diameter of the post-receiving chamber 32 is preferably less than the diameter of the interlock chamber 34. The post-receiving chamber also preferably includes a chamfered region 37, which is adjacent the threaded chamber 30.

One aspect of the present invention is that the implant 10 provides significant resistance to lateral (i.e., "tipping") forces. Accordingly, the interlock chamber 34 preferably has a depth D1 as measured from the top surface 24 that is greater than about 1 millimeter (see FIG. 1C). In the preferred embodiment, the interlock chamber has a depth of approximately 1.5 millimeters. Moreover, the post-receiving chamber 32 preferably has a depth D2 of greater than about 3 millimeters. In the preferred embodiment, the post-receiving chamber has a depth of approximately 4.0 millimeters.

FIGS. 2A–2D illustrates a dental component configured to mate with the implant 10 described above. The illustrated dental component is an abutment 38. As will be explained below, the abutment 38 can be formed into a variety of dental components, such as, for example, a healing cap, impression coping, a temporary healing abutment, and a final abutment. Preferably, the abutment 38 is made of dental grade titanium; however, other suitable materials such as plastic can be used.

Figure 2B:
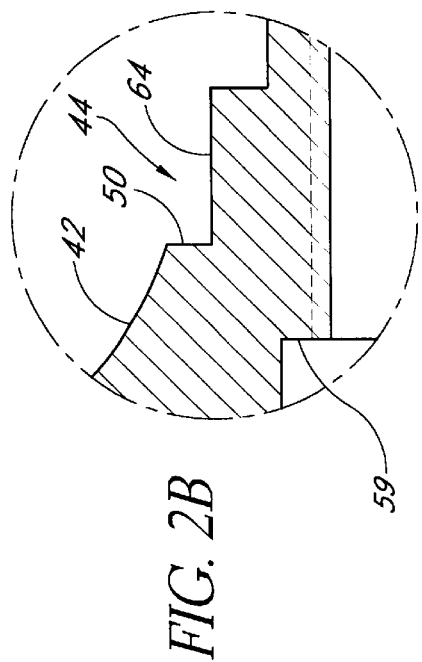
FIG. 2B is a detail view of the abutment of FIG. 2A.
Figure 2A:
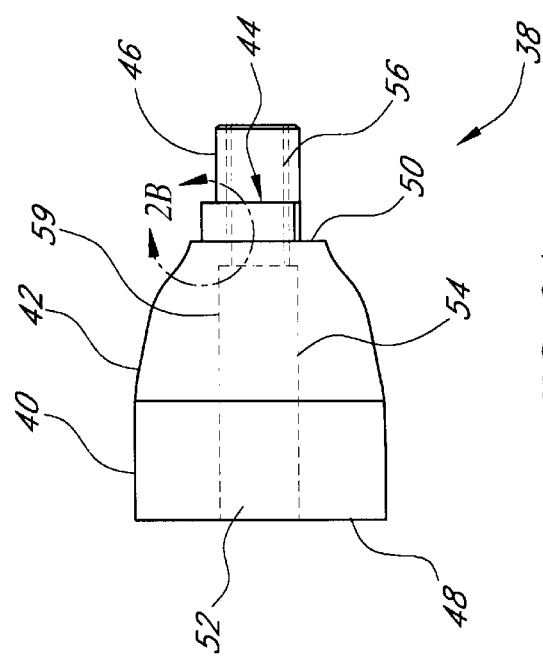
FIG. 2A is a side view of an abutment having certain features and advantages according to the present invention.
Figure 2C:
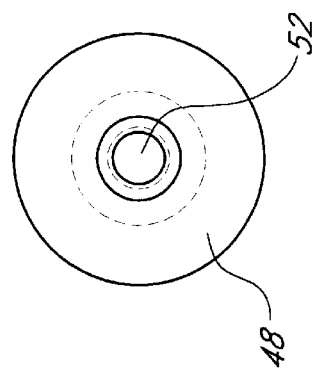
FIG. 2C is a top plan view of the abutment of FIG. 2A.

As best seen in FIG. 2A, the outer surface of the abutment 38 includes an upper region 40, a curved region 42, an interlock region 44, and a post 46. In the illustrated embodiment, the upper region 40 is substantially smooth, cylindrical and has a top surface 48 that is substantially flat. The curved region 42 connects the upper region 40 to a bottom surface 50, which is substantially flat.

The illustrated shape of the abutment 32 can be used as an healing abutment, which is typically used during the second healing period to shape the patient's gums. However, as mentioned above, the abutment 32 can be modified or otherwise formed into many different types of dental components. Therefore, it should be appreciated that the upper and curved regions 40, 42 of the abutment can be formed into any desirable shape.

As best seen in FIG. 2A, an inner bore 52 extends through the center of the abutment 38. The inner bore 52 is preferably divided into a first and second region 54, 56. The first region 54 has a diameter that is slightly larger than the diameter of the second region 56. Accordingly, a seat 59 is formed between the first and second regions 54, 56. The seat 59 supports a bolt 60 (see FIG. 3A), which will be described below. The second region 56 preferably includes internal capture threads that are preferably double threaded.

With continued reference to FIG. 2A, the bottom surface 50 is substantially flat and has a diameter approximately equal to the diameter of the top surface 24 of the implant 10. Extending from the bottom surface 50 is the interlock region 44, which is configured to fit within the interlock chamber 34 of the implant 10. Accordingly, as best seen in FIGS. 2B and 2D, the interlock area 44 includes a substantially cylindrical portion 63. The interlock area 44 also includes protrusions 64, which are configured to fit within the channels 36 of the implant. Accordingly, in the preferred embodiment, the protrusions 64 are arranged around the perimeter of the interlock area at approximately 120 degrees.

Below the interlock area 44 is the post 46. The post 46 is preferably substantially cylindrical and is configured to fit within the post-receiving chamber 32 of the implant.

Figure 3B:
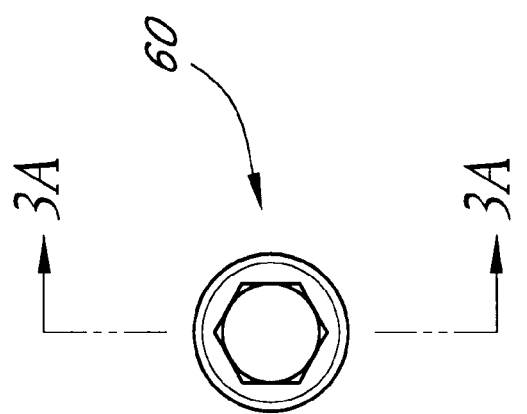
FIG. 3B is a top plan view of the coupling screw of FIG. 3A.
Figure 3A:
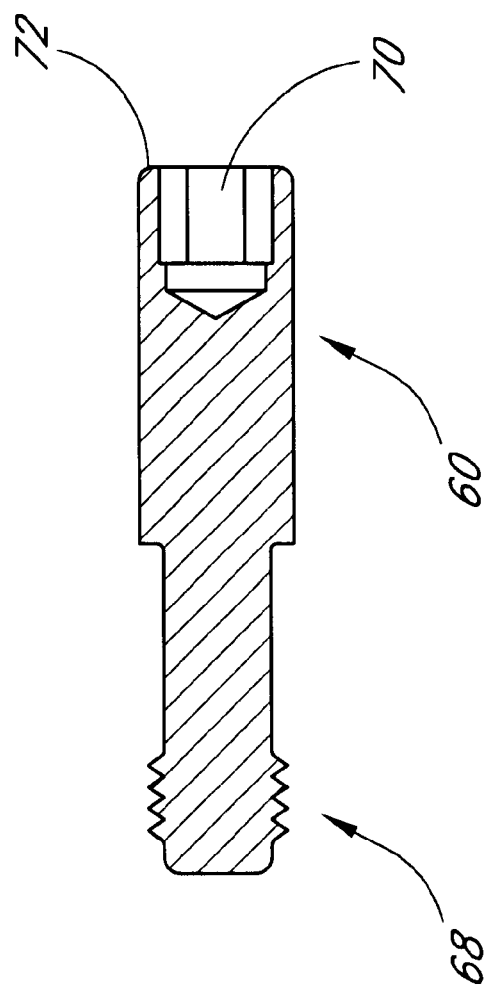
FIG. 3A is a cross-sectional view of a coupling screw having certain features and advantages according to the present invention.

Turning now to FIGS. 3A and 3B, the coupling screw 60 mechanically couples the abutment 38 to the implant 10. The coupling screw 60 is also preferably made of a dental grade titanium alloy; although other suitable materials can be used. The coupling screw 60 is sized and dimensioned to extend through the inner bore 52 of the blank abutment 38 and into the socket 28 of the implant 10. The coupling screw 60 has an externally threaded lower region 68 that passes through the internal capture threads of the abutment 38 and engages the threaded chamber 30 of the implant 10. The threads 68 of coupling screw 60 engage the capture threads so that the coupling screw 60 does not become disassociated as the abutment 38 is transferred and fitted to the patient's mouth.

The coupling screw also preferably includes a hexagonal recess 70 located on a top surface 72 of the screw 60. The hexagonal recess 70 allows for the insertion of a hexagonally shaped tool such as a conventional Allen® wrench to remove the coupling screw 60 from the implant body 10.

As mentioned above, during stage I surgery, the dental implant 10 is typically inserted into a pre-made hole formed in the patient's jawbone. A driving tool (not shown) is typically used to screw the implant into the pre-made hole. Accordingly, a distal end of the driving tool is preferably configured to mate with the interlock chamber 34 of the implant 10. That is, the distal end of the driver is preferably configured substantially the same as the interlock region 44 of the abutment 38 described above. When the driving tool is mated to the implant 10, the distal end of driver can be used to transmit torque to the implant through the interlock chamber 34 so as to drive the implant 10 into the pre-made hole. If the implant 10 is self-tapping, a particularly large amount of torque is required to drive the implant 10 into the bone. For conventional implants with hexagonal recesses, this large amount of torque can cause the implant to crack at the apexes of the hexagonal recesses. This reduces the strength of the implant and can cause fluids and bacteria to enter the implant.

An advantage of the illustrated implant 10 and mating abutment 38 is that when subjected to rotational forces the stress concentrations in the implant 10 and the abutment 38 are minimized. Stress concentrations refer to areas of large stress caused by geometric discontinuities (i.e., stress risers) and/or the application of large loads over a small area or at a point (e.g., at a corner or apex). Areas of large stress concentrations are often the starting point of material damage, which can ultimately lead to material failure by fracture (i.e., cracking). Thus, by minimizing stress concentrations, the durability of the implant 10 and the abutment 38 can be increase. The reduction in stress concentration derives from the particular preferred shape of the interlock chamber 34 of the implant 10 and the mating interlock region 44 of the abutment 38.

Figure 4A:
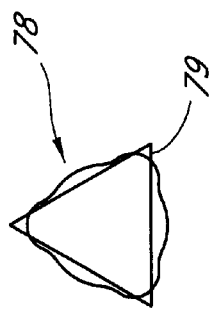
FIGS. 4A–C are schematic illustrations of preferred shapes of the interlock regions of the dental implant of FIG. 1A and the mating abutment of FIG. 2A.
Figure 4C:
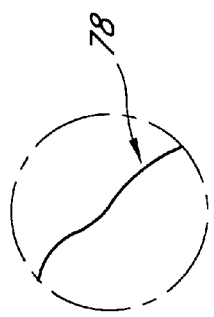
Figure 4B:
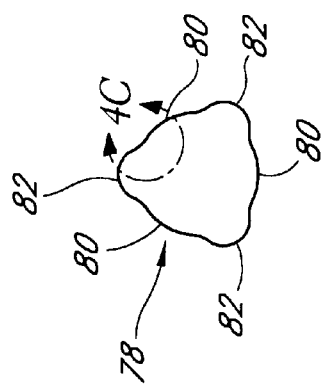

FIGS. 4A–C are schematic representations of the shape 78 of the interlock chamber 34 and the interlock region 44. FIG. 4A compares the shape 78 to a triangle 79. As seen in FIG. 4A, the shape 78 of the interlock region is in the form of an elliptically modified triangle 79. That is, the apexes and sides of the triangle are substantially rounded. As shown in FIGS. 4B and 4C, the shape 78 provides a smooth transition from the apex 82 to the sides 80. Accordingly, some of the anti-rotational stress is distributed away from the apexes 82 towards the relatively flatter side walls 80. These features help to reduce stress concentrations. Therefore, the interlock regions 34, 44 of the implant 10 and the blank abutment 38 (particularly the channels 36 and the protrusions 64 are less likely to chip and wear away as compared to prior art anti-rotational means. Moreover, the implant 10 is less likely to crack as compared to implants with hexagonal recesses, which tend to crank at the apexes of the hexagonal recess when subjected to large rotational loads (e.g., when a self-tapping implant is being threaded into the patient's jawbone).

Another advantage of the illustrated arrangement is that the abutment 38 and the implant 10 offer improved resistance to lateral or "tipping" forces. This improved resistance to lateral forces is due primarily to the depth of the interlock chamber 34 and the post-receiving chamber 32. The improved resistance to lateral forces also prevents the coupling screw 60 from loosening, thereby virtually eliminating movement between the implant 10 and the abutment 38.

Yet another advantage of the illustrated arrangement is that the interlock chamber of the implant 10 can be machined using a conventional end mill. That is, because of circular shape of the cylindrical portion 35, it can be machined with a conventional end mill. Moreover, the semi-circular channels can also be machined with a conventional end mill. This reduces the complexity of manufacturing especially as compared to the machining of a conventional hexagonal recess, which typically requires a reciprocating tool, such as, for example, a broach.

The illustrated arrangement of the implant 10 and abutment 38 also provides improved tactile confirmation that the blank abutment 38 is properly seated on the implant 10. That is because of the depth of the post-receiving chamber 32, the oral surgeon can feel the abutment 38 engaging the implant 10. This tactile confirmation is especially important for posterior prosthetics where visibility and working space are often compromised.

Figure 5B:
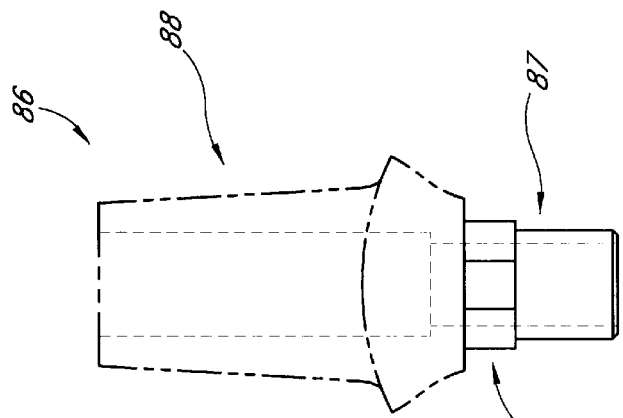
FIG. 5B is a front view of the final abutment of FIG. 4A.
Figure 5A:
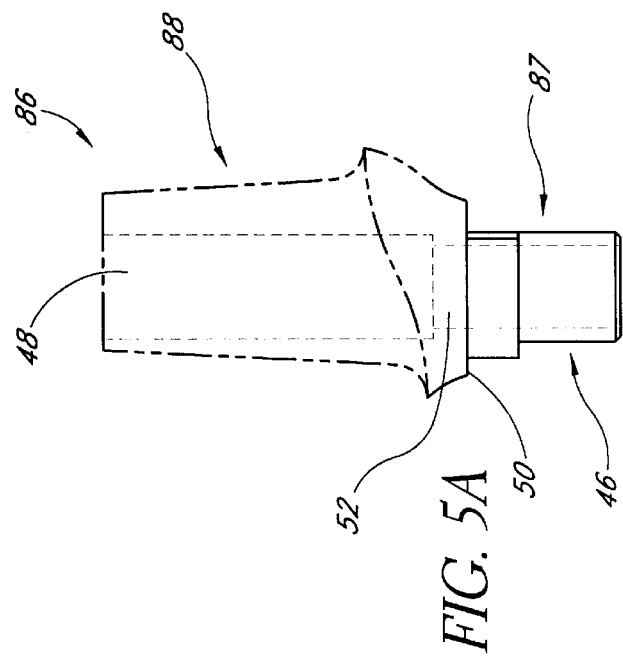
FIG. 5A is a side view of a final abutment having certain features and advantages according to the present invention.
Figure 5C:
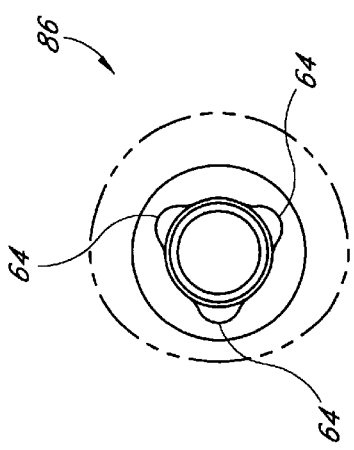
FIG. 5C is a bottom plan view of the final abutment of FIG. 4A.

FIGS. 5A–5C illustrate a final abutment 86 having certain features and advantages according to the present invention. The final abutment 86 is preferably made from a dental grade titanium allow, although other suitable materials can be use. The final abutment 86 can also be machined from the abutment 38 of FIGS. 2A–2D.

The lower region 87 of the final abutment 86 is substantially identical to the lower region of the blank abutment 38 described above. Accordingly, the lower region 87 comprises a lower surface 50, an interlock region 44 with protrusions 64, and a post 46. As with the blank abutment 38, the interlock region 44 with protrusions 64, and the post 46 that are sized and dimensioned to fit within the interlock chamber 34 and post-receiving chamber 32 of the implant 10.

Down the center of the final abutment 54 is an bore 48. The inner bore 48 is preferably divided into two regions: a first chamber 50 and a second region 52. Preferably, the diameter of the first chamber 50 is slightly larger than the second chamber 52. A screw passes through the screw receiving chamber 50 and engages the threads of the threaded region 52 and the first chamber 22 of the implant 10. Accordingly, the final abutment 54 can be permanently attached to the implant. Alternatively, the final abutment 54 could be cemented to the implant 10 using methods well known in the art.

The upper surface 88 of the final abutment 86 is formed to receive a prosthetic tooth. Accordingly, the prosthetic tooth (not shown) has an inner surface configured such that the prosthetic tooth can fit over the final abutment 86. The prosthetic tooth is typically cemented to the final abutment 86.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combination or subcombinations of the specific features and aspects of the embodiments may be made and still fall within the scope of the invention. Accordingly, it should be understood that various features and aspects of the disclosed embodiments can be combine with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A dental implant for supporting a dental prosthesis, the dental implant comprising a body portion and a top surface, the implant further comprising an internal cavity with an opening located at the top surface, the internal cavity comprising an interlock chamber having a depth measured from the top surface equal to a first distance, the interlock chamber comprising a non-threaded cylindrical portion and plurality of semi-circular channels arranged around a periphery of the cylindrical portion, and a threaded chamber that includes threads and is located below the interlock chamber, wherein the cylindrical portion has a first radius and the channels have a second radius, a ratio of the first radius to the second radius being between approximately 4:1 and 2:1; wherein the implant further includes a non-threaded post-receiving chamber that is located below the interlock chamber and above the threaded chamber, the post-receiving chamber having a depth measured from the top surface that is equal to a second distance.

2. The dental implant according to claim 1, wherein the ratio of the first radius to the second radius is approximately 3:1.

3. The dental implant according to claim 1, wherein the first distance is greater than 1 millimeter.

4. The dental implant according to claim 1, wherein the second distance is greater than approximately 3 millimeters.

5. The dental implant according to claim 4, wherein the first distance is greater than 1 millimeter.

6. The dental implant according to claim 1, wherein the interlock chamber comprises three channels.

7. The dental implant according to claim 6, wherein the three channels are arranged around the perimeter of the interlock chamber such that each of the channels are approximately 120 degrees apart from one another.

8. The dental implant according to claim 1, wherein the dental implant further includes a neck and a collar formed at least in part by a vertical side that has a length of approximately 2 millimeters.

9. The dental implant according to claim 1, wherein the top surface of the implant has a third radius and a ratio of the third radius to the second radius being between approximately 5:1 and 4:1.

10. The dental implant according to claim 9, wherein the ratio of the third radius to the second radius is approximately 4.5:1.

11. A prosthodontic assembly for installing a prosthetic tooth, the prosthodontic assembly comprising:
    a first prosthodontic component comprising a body portion and a top surface, the first prosthodontic component further comprising an internal cavity with an opening located at the top surface, the internal cavity comprising an interlock chamber having a depth measured from the top surface equal to a first distance, the interlock chamber comprising a non-threaded cylindrical portion with a plurality of semi-circular channels arranged around a perimeter of the cylindrical portion, a non-threaded post-receiving chamber that is located below the interlock chamber, the post-receiving chamber having a depth measured from the top surface that is equal to a second distance, and a threaded chamber that includes threads and is located below the post-receiving chamber, wherein the cylindrical portion has a first radius and the channels have a second radius, a ratio of the first radius to the second radius being between approximately 4:1 and 2:1.
    a second prosthodontic component comprising an interlock area comprising a plurality of semi-circular protrusions configured to mate with channels of the first prosthodontic component.

12. The prosthodontic assembly according to claim 11, wherein the ratio of the first radius to the second radius is approximately 3:1.

13. The prosthodontic assembly according to claim 11, wherein the first distance is greater than 1 millimeter.

14. The prosthodontic assembly according to claim 11, wherein the second prosthodontic component further comprises a post configured to mate with the post-receiving chamber of the first prosthodontic component.

15. The prosthodontic assembly according to claim 14, wherein the second distance is greater than 3 millimeters.

16. The prosthodontic assembly according to claim 15, wherein the first distance is greater than 1 millimeter.

17. The prosthodontic assembly according to claim 11, wherein the interlock chamber comprises three channels and the interlock area comprises three protrusions.

18. The prosthodontic assembly according to claim 11, wherein the three channels are arranged around the perimeter of the interlock chamber such that each of the channels are approximately 120 degrees apart from one another and the three protrusions are correspondingly arranged around the perimeter of the interlock area such that each of the protrusions are approximately 120 degrees apart.

19. The prosthodontic assembly according to claim 11, wherein the first prosthodontic component further includes a neck and a collar formed at least in part by a vertical side that has a length of approximately 2 millimeters.

20. The prosthodontic assembly according to claim 11, wherein the top surface of the implant has a third radius and a ratio of the third radius to the second radius being between approximately 5:1 and 4:1.

21. The dental implant according to claim 20, wherein the ratio of the third radius to the second radius is approximately 4.5:1.

* * * * *